(12) United States Patent
Vancamberg et al.

(10) Patent No.: US 11,918,392 B2
(45) Date of Patent: Mar. 5, 2024

(54) VISION-GUIDED BIOPSY SYSTEM AND METHOD FOR MAMMOGRAPHY

(71) Applicant: GE Precision Healthcare LLC, Wauwatosa, WI (US)

(72) Inventors: Laurence Vancamberg, Poissy (FR); Serge Muller, Guyancourt (FR); Serge Calisti, Marseilles (FR)

(73) Assignee: GE Precision Healthcare LLC, Milwaukee, WI (US)

( * ) Notice: Subject to any disclaimer, the term of this patent is extended or adjusted under 35 U.S.C. 154(b) by 0 days.

(21) Appl. No.: 17/126,472

(22) Filed: Dec. 18, 2020

(65) Prior Publication Data
US 2022/0192614 A1    Jun. 23, 2022

(51) Int. Cl.
*A61B 6/00* (2006.01)
*A61B 6/02* (2006.01)
*A61B 6/04* (2006.01)

(52) U.S. Cl.
CPC .............. *A61B 6/425* (2013.01); *A61B 6/022* (2013.01); *A61B 6/0414* (2013.01); *A61B 6/0435* (2013.01); *A61B 6/4458* (2013.01); *A61B 6/466* (2013.01); *A61B 6/502* (2013.01); *A61B 6/54* (2013.01)

(58) Field of Classification Search
CPC ..... A61B 6/022; A61B 6/0414; A61B 6/0435; A61B 6/4458; A61B 6/466; A61B 6/502; A61B 6/54; A61B 10/0041; A61B 10/0233; A61B 90/11; A61B 90/17; A61B 90/361; A61B 34/35; A61B 34/72
See application file for complete search history.

(56) References Cited

U.S. PATENT DOCUMENTS

| | | | |
|---|---|---|---|
| 6,459,925 B1 * | 10/2002 | Nields | A61B 8/4416 600/440 |
| 6,592,257 B1 | 7/2003 | Heidsieck et al. | |
| 10,383,654 B2 * | 8/2019 | Yilmaz | A61B 34/30 |

(Continued)

OTHER PUBLICATIONS

Janz, A. et al., "Position Determination of a Robot End-Effector Using a 6D-Measurement System Based on the Two-View Vision", Open Journal of Applied Sciences, 2013, 3, 393-403.

(Continued)

*Primary Examiner* — Dani Fox
*Assistant Examiner* — Soorena Kefayati (57) ABSTRACT

A mammography system includes a biopsy guidance system that employs a simplified robot arm support, to enable previously unusable locations for the mounting of the biopsy device directly to the mammography system, such as on a compression paddle, combined with a vision guidance and control system. The vision system operates to determine the position of the biopsy device and the biopsy needle tip, as well as to control the movement/operation of the biopsy guidance system, such as movement to the final end-pose or pre-firing position of the biopsy device to perform the biopsy procedure. The vision system utilizes one or more cameras to visually determine the position the biopsy device relative to a region of interest being biopsied within the required tolerances for the biopsy procedure without the need for precise positional information to be provided by the biopsy guidance system to the mammography system.

20 Claims, 7 Drawing Sheets

(56) References Cited

U.S. PATENT DOCUMENTS

| | | | | |
|---|---|---|---|---|
| 2006/0052693 | A1* | 3/2006 | Tynes | G16H 30/40 |
| | | | | 600/424 |
| 2007/0225600 | A1* | 9/2007 | Weibrecht | A61B 6/502 |
| | | | | 600/429 |
| 2008/0103387 | A1* | 5/2008 | Gross | A61B 6/4417 |
| | | | | 600/564 |
| 2009/0171244 | A1* | 7/2009 | Ning | A61B 6/0435 |
| | | | | 378/37 |
| 2010/0054402 | A1* | 3/2010 | Fischer | A61B 6/542 |
| | | | | 378/37 |
| 2010/0104063 | A1* | 4/2010 | Bindra | A61B 90/17 |
| | | | | 378/37 |
| 2011/0087132 | A1* | 4/2011 | DeFreitas | A61B 10/0233 |
| | | | | 378/62 |
| 2012/0022358 | A1* | 1/2012 | Fischer | A61B 6/502 |
| | | | | 600/407 |
| 2012/0150034 | A1* | 6/2012 | DeFreitas | A61B 6/5247 |
| | | | | 250/363.04 |
| 2013/0223590 | A1* | 8/2013 | Rafaeli | A61B 6/502 |
| | | | | 378/37 |
| 2016/0007940 | A1* | 1/2016 | Khamaisi | A61B 6/4266 |
| | | | | 600/424 |
| 2016/0143693 | A1* | 5/2016 | Yilmaz | A61B 6/502 |
| | | | | 606/130 |
| 2016/0183887 | A1* | 6/2016 | Toba | A61B 6/025 |
| | | | | 600/424 |
| 2016/0310215 | A1* | 10/2016 | Palma | A61B 34/10 |
| 2018/0168523 | A1* | 6/2018 | Vancamberg | A61B 10/0233 |
| 2019/0125289 | A1* | 5/2019 | Van Es | A61B 6/547 |
| 2019/0154595 | A1* | 5/2019 | Rempel | A61B 6/4417 |
| 2019/0209106 | A1* | 7/2019 | Bechtold | A61B 6/54 |
| 2020/0000442 | A1 | 1/2020 | Vancamberg et al. | |
| 2020/0337667 | A1* | 10/2020 | Arai | A61B 8/403 |
| 2021/0298702 | A1* | 9/2021 | Konno | A61B 6/502 |

OTHER PUBLICATIONS

Abu Hassan. M.F. et al., "3D Distance Measurement Accuracy on Low-Cost Sterero Camera", Sci.Int. (Lahore), 29(3), 599-605, 2017.
Lisowski, W. et al., "A Low-Cost Vision System in Determination of a Robot End-Effector's Positions", Pomiary Automatyka Robotyka, ISSN 1427-9126, R 21, Nr Apr. 2017, 5-13, DOI: 10.14313/PAR_226/5.
Bleser, G. et al., "Online camera pose estimation in partially known and dynamic scenes", IEEEConference Paper 2006.
EP application 21213055.3 filed Dec. 8, 2021—extended Search Report dated May 2, 2022; 11 pages.

* cited by examiner

VISION-GUIDED BIOPSY SYSTEM AND METHOD FOR MAMMOGRAPHY

The present disclosure relates generally to mammography systems and devices, and more specifically to guidance systems utilized with a mammography device.

BACKGROUND OF THE DISCLOSURE

Embodiments of the invention relate generally to X-ray medical imaging, and more particularly to systems and methods to perform biopsy exams guided by a stereotactic mammography, or digital breast tomosynthesis (DBT). Spectral mammography (SM) can also be used to guide the biopsy exam, with or without contrast agent injection, either in 2D (CESM guided biopsy) or in 3D (CEDBT guided biopsy).

X-ray mammography (MG) is an X-ray imaging modality used to scan breasts for screening, diagnosis and/or interventional examinations. The effectiveness of X-ray mammography is affected by numerous factors, one of which is the two-dimensional (2D) rendering of images obtained.

Alternative systems to 2D X-ray mammography are also known for breast imaging. For example, a digital breast tomosynthesis (DBT) or mammography-tomography (mammo-tomo) system is a dedicated mammography system that acquires several (e.g., tens of) angularly offset projection X-ray images and uses the resulting X-ray image data to reconstruct three-dimensional (3D) image datasets.

When the 3D image datasets of the breast have been produced, they are utilized to guide a biopsy device employed with the DBT system into the breast to obtain a biopsy of the region of interest (ROI) identified within the 3D image datasets. In DBT systems, the biopsy device is disposed directly on the DBT system in order to be able to perform the biopsy utilizing the 3D image dataset to guide the biopsy device to the ROI. Because the areas in the breast constituting the ROI can be quite small, the movement of the biopsy device from the idle or stand-by position into the breast to reach the biopsy pre-fire position requires precise movement and positioning of the biopsy device. To achieve this level of accuracy, which is normally required to be +/−1 mm for the end of the biopsy device relative to the ROI, determining the exact initial localization, i.e., the spatial position and angulation, of the end pose segment/end effector of the biopsy guidance system holding the interventional device, e.g., a biopsy device, and the needle itself, or any other interventional tool used in mammography, presents a challenging problem in mammography biopsy procedures.

To address this issue in prior art biopsy guidance system, the biopsy guidance system is constructed as a dedicated robotic arm located on the mammography system that is formed with a robust mechanical structure utilizing heavy machined metal parts interconnected by micromotors, e.g., micro servomotors, and associated rotary encoders to move the various components of the biopsy guidance system in a precisely controlled manner. The structure of the biopsy guidance system is mounted to the gantry to support the weight of the biopsy guidance system while allowing the biopsy device to move within the area relative to the gantry in which the biopsy is to be performed.

With this oversize structure, the biopsy guidance system can be accurately controlled by the operation of the servomotors using signals from the mammography system to the rotary encoders to perform the biopsy procedure. The rotary encoders provide a signal(s) to the mammography system concerning the initial position of the end effector of the biopsy guidance system to which the biopsy device and its needle is mechanically mounted. Based on the known location of end effector and the known location of the ROI in the 3D image dataset reconstructed from the X-ray image data, the mammography system controls the movement of the robotic arm of the biopsy guidance system using signals sent to the rotary encoders to operate the servomotors and accurately position the end effector (biopsy device) and needle at any position required to perform the biopsy procedure.

While able to provide precise locations for the components of the biopsy guidance system and to enable accurate positioning of the end effector/needle to perform the biopsy procedure, these prior art robotic arm biopsy guidance system have a number of significant drawbacks. Specifically, all of the required information regarding the position and movement of the biopsy device/needle during a biopsy procedure is provided directly from the biopsy guidance system itself. As a result, the components for the robotic arms and biopsy devices/needles in the prior art have to be precisely machined in order to provide the precise position data of the biopsy device to the mammography system with the required tolerances for the biopsy procedure. As the tolerance of the needle position is +/−1 mm for the biopsy procedure, all of the components for the biopsy guidance system must be manufactured to enable the system to operate within this tolerance limit.

In addition, to enable the biopsy guidance system components and biopsy device to stay within this tolerance limit over repeated uses of the system, the components need to be formed of suitable materials that will not deform during use to maintain the accuracy of the positional information provided to the mammography system. As such, the materials utilized are selected from various metals and/or metal alloys having desirable material properties that allow the materials to retain their shape over multiple procedures. However, these types of materials are difficult to machine as a direct result of their desirable material properties. In addition, the size of the machined components utilized to enhance the ability of the selected material to retain its shape results in components that are very dense and heavy, requiring significant mounting structures added to the mammography system to accommodate the weight of the biopsy system.

Furthermore, as a result of the selected materials and size and associated weight of the components of the biopsy guidance system and device, the movement mechanisms disposed between the components, e.g., the servomotors and rotary encoders, must be selected to be sufficiently robust and powerful to accommodate for these aspects of the biopsy guidance system, which in turn requires a larger power supply and more complex control system connections with the mammography system for proper operation of the biopsy guidance system and device.

As a result, it is desirable to develop a biopsy guidance system and device that can provide the precision required for the performance of an interventional procedure using a mammography system, but without the significant drawbacks currently present in the prior art biopsy guidance systems and devices utilized for this purpose.

SUMMARY OF THE DISCLOSURE

According to one aspect of an exemplary embodiment of the disclosure, a biopsy guidance system is provided that employs a simplified robot arm support, which is manufactured within significantly wider mechanical tolerances than required for prior art biopsy guidance system robotic arms, combined with a vision guidance and control system. The vision system operates to determine the position of the robotic arm, such as the last segment of the robotic arm or the end effector, or of a biopsy tool and/or the biopsy needle tip mounted to the end effector, as well as to control the movement/operation of the biopsy guidance system, such as at the final end-pose or pre-firing position of the biopsy device to perform the biopsy procedure. The vision system utilizes one or more cameras to visually determine the position the robotic arm, e.g., one of the segments of the robotic arm such as the end effector, or the biopsy device or the biopsy device needle within the required tolerances for the biopsy procedure without the need for precise positional information to be provided to the mammography system by highly precise mechanical systems on the robotic arm.

The biopsy guidance system, according an exemplary embodiment of the disclosure, incorporates a motor-controlled robot arm including a number of independently movable components or segments, terminating in an end effector forming the last segment of the robotic arm, and a vision system for visually determining the position of one or more segments of the robotic arm, such as the end effector, or the position of the biopsy device or needle/needle tip. The vision system includes at least one camera that is capable of determining and providing information to the mammography system regarding the exact location of one or more of the different segment(s) of the robotic arm, such as the end effector, the biopsy device and/or the tip of the needle forming a part of the biopsy device relative to the mammography system, as well as to the ROI determined within the 3D image dataset reconstructed from the X-ray image data obtained by the mammography system. By visually ascertaining the location of the end effector using the camera at the initial localization of the end effector, and optionally through the movement of the end effector to the pre-firing position, the biopsy guidance system can use this visual determination from the camera to precisely locate and guide the position of the end effector within the required tolerance (e.g., +/−1 mm) for the biopsy procedure.

The construction of the biopsy guidance system including the vision system is greatly simplified as the precise determination of the localization of the end effector is not determined by the successive segments of the robotic arm and the end effector itself, but by the vision system disposed externally to the end effector. This negates the need for the heavy, precisely machined components, high power servomotors and robust support structures required by prior art biopsy systems. As such, the construction of the robotic arm of the biopsy guidance system is only required to closely control the movement of the end effector, which can be performed by less complex arm structures and motive mechanisms connected to the end effector, as the monitoring and guidance of the position of one or more segments of the robotic arm, e.g., the end effector, the biopsy device or the tip of the needle is provided by the external vision system.

In addition, the location of the vision system components, e.g., the cameras, is determined in light of the structure of the mammography system with which the vision system is utilized, as well as the known movement pattern of the components of the mammography system in the performance of the biopsy procedure. In doing so, the camera placement provides an optimal field of the view for the vision system of the end effector and optionally the patient breast, such as for collision management, while also accommodating for the presence of other components of the mammography system and obstructions, such as the technician and patient, among others. Further, while a single camera can be utilized as the vision system to determine the precise location of the end effector, the use of two or more cameras mounted to the mammography system externally of the end effector increases the accuracy of the location determination for the end effector by enabling stereoscopic/computer stereo vision methods to be employed.

According to another aspect of an exemplary embodiment of the disclosure, with the simplified construction of the robotic arm and end effector, there are an increased number of location options for the attachment of the robotic arm to the mammography system. More specifically, as the lighter weight robotic arm/end effector can be mounted to the mammography system without the need for robust mounting structures, the robotic arm/end effector can be disposed on previously unusable areas of the mammography system, such as the compression plate or movable compression carriage to which the compression plate is mounted.

According to still another aspect of an exemplary embodiment of the present disclosure, a mammography system operable in an imaging mode and in an interventional/biopsy mode includes a gantry disposed movably disposed on a support surface and including an X-ray source, an X-ray detector alignable with the X-ray source, and a compression paddle moveable relative to the detector to secure a patient breast therebetween, a biopsy system mounted to the gantry, the biopsy system including a movable robotic arm secured to the gantry and having a number of independently movable components or segments that terminate at an end effector disposed on the robotic arm opposite the gantry. The biopsy system additionally includes a biopsy device mounted to the end effector opposite the robotic arm segments and includes a needle operably engaged with a firing mechanism within the biopsy device to actuate the needle to obtain a biopsy sample. The mammography system further includes a control system operably connected to the gantry to control the operation of the X-ray source and X-ray detector to generate X-ray image data in an imaging mode for the mammography system, and to control the operation of the biopsy system in an interventional/biopsy mode for the mammography system, the control system including a central processing unit and interconnected database for processing the X-ray image data from the detector, a display operably connected to the control system for presenting information to a user, and a user interface operably connected to the control system to enable user input to the control system and a vision guidance system disposed on the gantry and operably connected to the control system; the vision system including at least one camera operable to generate images of one or more of the segments of the robotic arm, the end effector, the biopsy device and/or the needle, and to guide the movement of the biopsy system.

According to still another aspect of an exemplary embodiment of the present disclosure, a method for guiding a biopsy device while performing a biopsy procedure includes the steps of providing a mammography system having a gantry disposed movably disposed on a support surface and including an X-ray source, an X-ray detector alignable with the X-ray source, and a compression paddle moveable relative to the detector to secure a patient breast therebetween, a biopsy system mounted to the gantry, the biopsy system including a movable robotic arm secured to the gantry including a number if independently movable segment terminating at an end effector disposed on the robotic arm opposite the gantry, and optionally a biopsy device and a needle operably connected to the end effector opposite the robotic arm, a control system operably connected to the gantry to control the operation of the X-ray source and X-ray detector to generate X-ray image data in an imaging mode for the mammography system, and to control the operation of the biopsy guidance system in an interventional/biopsy mode for the mammography system, the control system including a central processing unit and interconnected database for processing the X-ray image data from the detector, a display operably connected to the control system for presenting information to a user, and a user interface operably connected to the control system to enable user input to the control system and a vision guidance system disposed on the gantry and operably connected to the control system, the vision system including at least one camera operable to generate images of one or more of one or more of the segments of the robotic arm, such as the end effector, the biopsy device or needle and/or needle tip to guide the movement of the biopsy system, positioning a patient breast between the detector and the compression plate, obtaining a number of images of the robotic arm, end effector, and the biopsy device or needle with the vision guidance system to determine the position of the needle relative to the patient breast, and moving the robotic arm/biopsy system under the direction of the vision guidance system.

These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Figure 1:
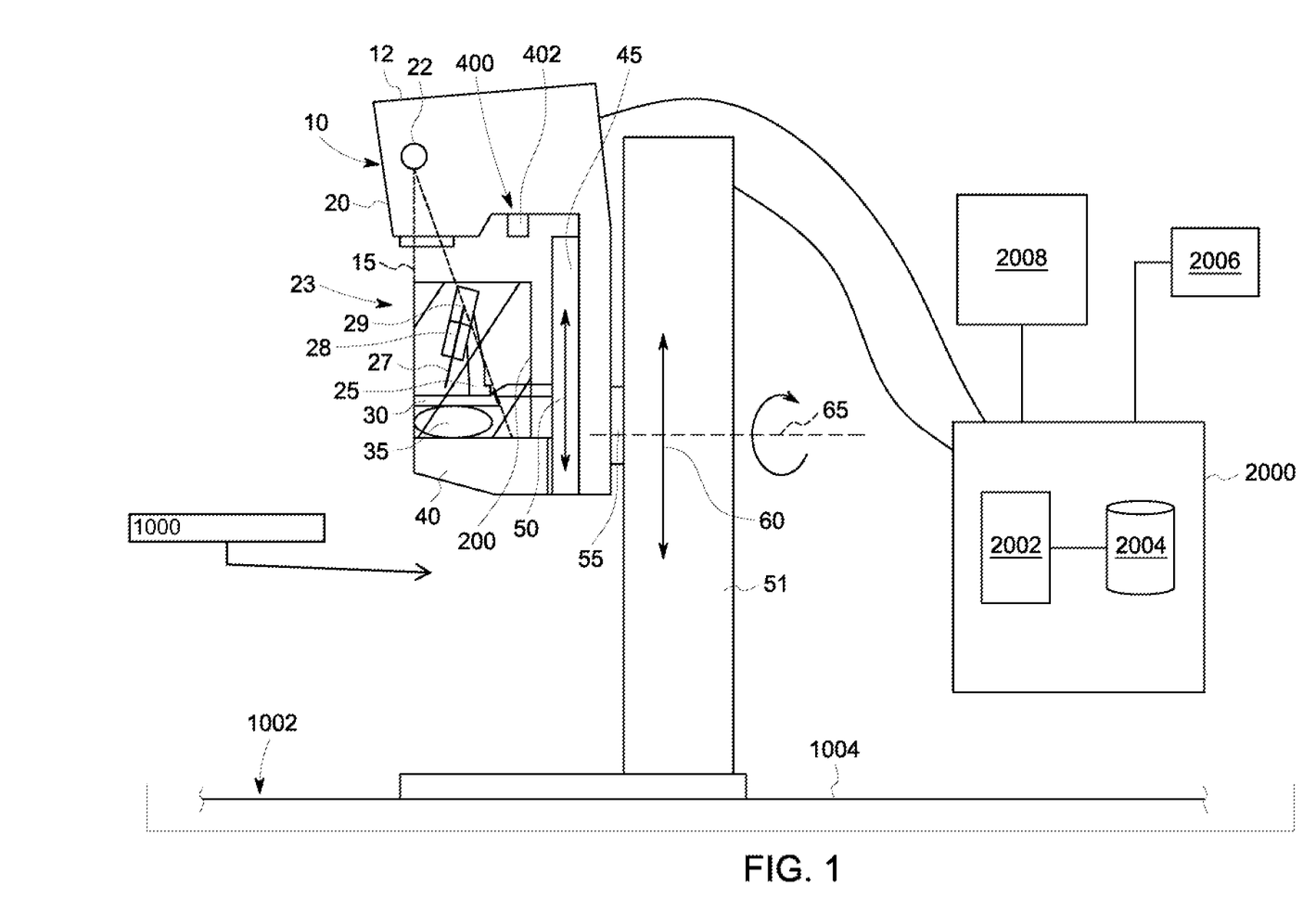
FIG. 1 is a schematic side elevational view of a mammography system including a vision-guided biopsy system in accordance with an exemplary embodiment of the invention.

Referring now to FIG. 1, a mammography system 1000 is schematically illustrated. The system 1000 represents any system operable to perform mammography (MG), i.e., an X-ray imaging modality used to scan breasts for screening, diagnosis and/or interventional examinations, such as 2D stereotactic mammography, i.e. two X-ray projection images of the breast acquired at different angle of the X-ray source, or digital breast tomosynthesis (DBT) guided biopsy exam that acquires several (e.g., tens of) angularly offset projection images and reconstructs three-dimensional (3D) image datasets from the acquired X-ray image data. Spectral mammography can also be used either in 2D or in 3D. When the image datasets of the breast have been produced, they are utilized to guide a biopsy device employed with the mammography system into the breast to obtain a biopsy of the region of interest (ROI) identified within the 3D image datasets.

In addition, it is important to note that multiple variations of the basic functions and components of the mammography system 1000 described here exist, but while having different implementations, the functions and elements presented in the following manner regarding the disclosed mammography system 1000 are intended to broadly cover other configurations and types of mammography systems 1000, such as, but not limited to those disclosed in US Patent Application Publication No. US2020/0000442, entitled System And Method For Selecting A Patient Position And An Equipment Configuration For A Medical Procedure, U.S. Pat. No. 6,592,257, entitled Detachable Device For Radiological Digital Imaging, and/or the GE Healthcare Senographe Pristina Mammography System, whose disclosures, structures and method(s) of operation are each expressly incorporated herein by reference for all purposes.

As shown in FIG. 1, the mammography system 1000 generally illustrated includes a stand 51 disposed on a support surface 1002, such as a floor 1004, that functions to support a gantry 10 that includes the imaging components of the mammography system 1000. The system 1000 additionally includes a control system 2000 that can be incorporated as a portion of the stand 51, or can be spaced from the stand 51, or a combination thereof. The control system 2000 is operably connected to the stand 51 and to the imaging components of the system 1000 on the gantry 10, and includes a processing unit 2002 with associated electronic data storage elements/databases 2004 in order to receive and process X-ray image data from the imaging components (X-ray source 22 and detector 40) on the gantry 10 to generate the image datasets and identify any ROIs present therein that require a biopsy procedure to be performed for further analysis of the ROI. The control system 2000 also includes a user input 2006, e.g., keyboard, mouse, touch screen, joystick, or other suitable manual control or input device, etc., for enabling control of the components of the system 1000 by a user and a display unit 2008 on which the operational status and/or 3D image datasets, among other information, can be visually presented to the user.

The stand 51 houses a translation mechanism 60 that is operably connected to the gantry 10 for the system 1000 via a suitable connection 55. The translation mechanism 60 is operable to move the gantry 10 vertically with respect to the stand 51 in order to position the gantry 10 at the appropriate height to accommodate the dimensions of the patient on which the system 1000 is being utilized. The translation mechanism 60 is also operable to rotate the gantry 10 relative to the stand 51 about a horizontal axis 65 centered on the connection 55 in order to position the gantry 10 rotationally with regard to the patient 340 (FIG. 3B) as necessary.

The gantry 10 includes a generally C-shaped body 12 that includes a casing 20 located at one end. Within the casing 20 is disposed an X-ray source 22 operable to emit X-rays 15 out of the casing 20. The X-ray source 22 is located opposite a sensor table/detector 40 disposed on and mounted to the opposite end of the body 12. In this configuration, regardless of the vertical and/or rotational orientation of the gantry 10, such as to position the X-ray source 22 and detector 40 relative to the patient breast 35 to obtain X-ray images at various orientations, such as for craniocaudal (CC) or mediolateral oblique (MLO) views, among others, the X-ray source 22 is disposed in alignment with the detector 40. In this position, the detector 40 is capable of receiving the X-rays 15 from the X-ray source 22 that pass through the portion of the patient, i.e., patient breast 35, located between the X-ray source 22 and the detector 40 in order to generate X-ray image data for transmission to the control system 2000 of the mammography device/system 1000 to create a 2D mammographic image, or optionally a 3D mammographic image or reconstructed volume if multiple X-ray views are utilized such as in DBT, for viewing by a physician, among other known methods.

Additionally, the X ray source 22 can be attached to the body 12 of the gantry 10 to rotate and/or move independently of the gantry 10 and detector 40 in order to enable the X-ray source 22 to take X-ray images of the patient breast 35 at various angles relative to the detector 40, e.g., between +/−60°. The images obtained between these angles for the X-ray source 22 can be used either for creation of stereoscopic images in a biopsy procedure using the system 1000 or for DBT when operating the system 1000 in an imaging mode, though the system 1000 can also be operated in a DBT or similar mode to provide biopsy guidance.

In order to maintain the position of the patient breast 35 stationary during the imaging and/or biopsy procedures, the gantry 10 also includes a compression paddle 30 thereon and spaced from the detector 40. The paddle 30 is attached to a paddle support mechanism 45 located on and/or within the body 12 that positions the paddle 30 directly over and in alignment with the detector 40. The paddle support mechanism 45 is operable within the body 12 at any rotational or vertical position of the body 12 to move the paddle 30 in a line either towards or away from the detector 40. The mechanism 45 can have any of a number of different configurations, but in the illustrated embodiment of FIG. 1 has the form of a compression screw mechanism 50. The compression screw mechanism 50 is operable to move the paddle 30 into engagement with the patient breast 35 to exert a predetermined pressure/compression on the breast 35 to retain the breast 35 in a stationary position between the paddle 30 and the detector 40 during imaging and biopsy procedures.

Also disposed on the gantry 10 is a biopsy system 23. The biopsy system 23 includes a robotic arm 25, best shown in FIG. 5, that is moveably mounted to the gantry 10, optionally in a removable manner. In the illustrated exemplary embodiment, the robotic arm 25 includes a number of different and independently articulatable component sections or segments 33 connected to one another and to various motive mechanisms/motors 34 that provide a number of different degrees of movement to the robotic arm 25 to enable the robotic arm 25 to be positioned at the desired orientation and spacing relative to the patient breast 35 positioned between the compression paddle 30 and the detector 40

Figure 5:
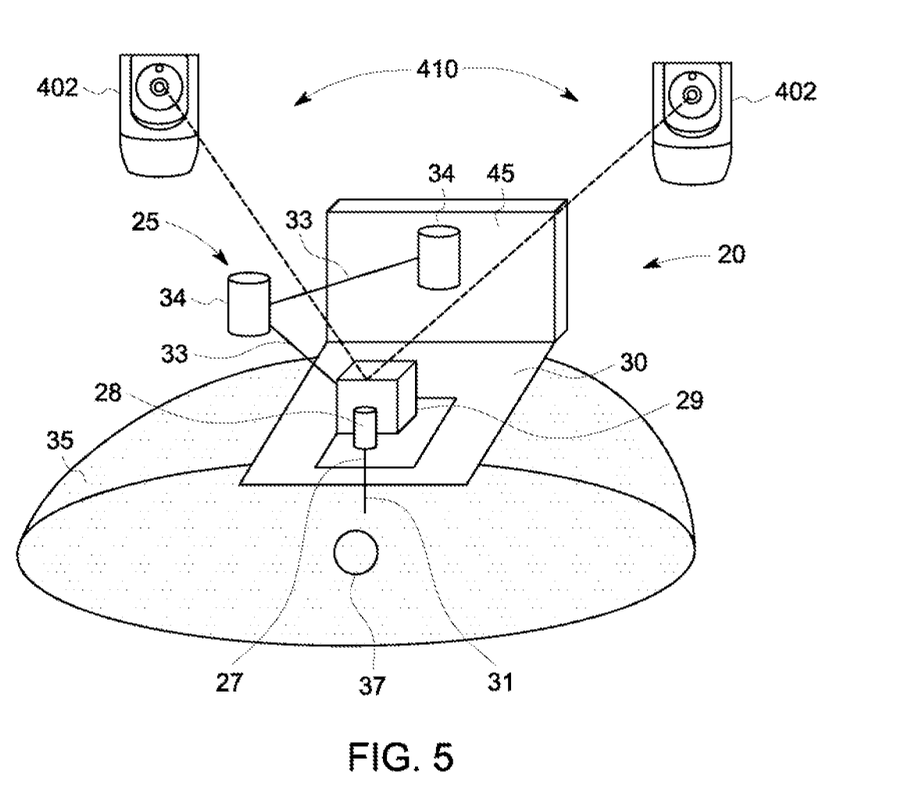
FIG. 5 is an isometric schematic view of a biopsy device of the vision guided biopsy system mounted to a compression paddle.

The robotic arm 25 extends away from the compression paddle 30 and terminates at an end effector 29, which in the illustrated exemplary embodiment is the moveable component on or segment 33 of the robotic arm 25 located opposite the paddle 30 (FIG. 5). The end effector 29 supports a biopsy device 28 thereon that includes a biopsy needle 27 secured thereto, where the needle 27 has a tip 31 disposed opposite the biopsy device 28. The biopsy device 28 can be operated to move or fire the needle 27 with regard to the biopsy device 28 in a manner that enables the needle 27 to obtain a biopsy of the patient breast 35. The range of movement of the robotic arm 25 allows the biopsy device 28 to be rotated at least +/−90° around an axis extending through the patient breast 35 and parallel to the axis of rotation for the sensor table/detector 40.

Opposite the biopsy device 28, in the illustrated exemplary embodiment the robotic arm 25 is mounted, optionally removably, to the gantry 10 to enable the robotic arm 28 to be entirely supported by the gantry 10. Further, the robotic arm 25 includes operating connections through the gantry 10 between the motive mechanisms 34, e.g., servomotors, and other localization means such as potentiometers and brakes (not shown), among others, that are disposed on the end effector 29 and other components/segments 33 of the robotic arm 28 and the control system 2000 to enable control of these mechanisms 34 via the control system 2000 to position the biopsy device 28 where desired. While the robotic arm 25 can be mounted to the gantry 10 in any suitable position to place the end effector 29, the biopsy device 25 and needle 27 in close proximity to the patient breast 35, such as on the detector 40, in the illustrated exemplary embodiment of FIG. 1 the robotic arm 25 is secured to the compression paddle 30. In this position, the robotic arm 25, and biopsy device 28 disposed thereon, can be moved along with the compression paddle 30 by the paddle support mechanism 45.

Referring now to FIGS. 1-3B, also forming a portion of the biopsy system 23 is a vision motion guidance and control system 400 including one or more light imaging devices, including, but not limited to a structure light system, an infra-red (IR) depth sensor, or video cameras 402. The vision system 400 is operably controllable by the control system 2000 to obtain images of the biopsy device 28 as well as component parts thereof, including the end effector 29, needle 27 and needle tip 31. The images obtained by the cameras 402 are used by the control system 2000 in order to determine the exact location of the end effector 29, or any other segment 33 of the robotic arm 25, the biopsy device 28 and/or the needle 27 or needle tip 31 to determine the required movement of the device 28 towards the patient breast 35 in the performance of a biopsy procedure. As the system 1000 has already generated a 3D image dataset representing the patient breast 35 from the X-ray image data obtained during an imaging procedure, thus determining the location of one or more ROIs within the patient breast 35 to be biopsied, the system 1000 employs the image data, e.g., visual image data, from the cameras 402 of the vision system 400 to locate the exact position of the robotic arm 25 or one or more segments 33 thereof, including the end effector 29, and/or the biopsy device 28/needle 27/tip 31 relative to the ROI 37 (FIG. 5) with a high degree of accuracy and subsequently precisely direct the movement of the robotic arm 25 in performing the biopsy procedure. The accuracy of the vision system 400 negates the need for precise mechanical control systems or mechanisms in the robotic arm 25. The vision system 400 can precisely locate one or more segments 33 of the robotic arm 25, such as the end effector 29, such that only the movement of the particular segment 33, e.g., end effector 29, needs to precisely controlled by the control system 2000 within the tolerances for the biopsy procedure to properly locate the biopsy device 28/needle 27/needle tip 31 at the required location.

In an exemplary embodiment, the cameras 402 in vision system 400 are formed as camera pairs 410 in order for the vision system 400 to obtain images from the camera pairs 410, e.g. a synchronized RGB camera, that can be used by the control system 2000 in a stereoscopic method or process to generate a 3D image of the location of the robotic arm 25 and/or the biopsy device 28/needle 27/tip 31 in order determine the exact position of the robotic arm 25/biopsy device 28 relative to the patient breast 35/ROI 37. With this precise localization/positional knowledge of the robotic arm 25/end effector 29, and thus of the biopsy device 28/needle 27/tip 31 mounted thereto, the control system 2000 can precisely control the movement/operation of the robotic arm 25 within the required position tolerances to properly locate the biopsy device 28 where required during the performance of a biopsy procedure.

In a further exemplary embodiment, at least two camera pairs 410 (FIGS. 4A-4B) are utilized in the vision system 400 to provide images from the camera pairs 410 capable of being utilized both individually and combined with one another in a stereoscopic imaging process performed by the control system 2000 in a known manner to generate a 3D image of the precise location of the robotic arm 25 and/or end effector 29, including the location of the biopsy device 28, needle 27 and/or needle tip 31 mounted to the end effector 29, and of the patient breast 35.

In all of the aforementioned embodiments, the image data from the vision system 400 can be used by the control system 2000 to locate and determine the exact position of the robotic arm 25 and/or segment(s) 33/end effector 29 relative to the ROI 37, and in particular the location of the end effector 29, and thus the biopsy device 25 and associated needle 27, e.g., the tip 31 of the needle 27, to guide or direct movement of the robotic arm 25 in either a continuous or intermittent manner during all or any portion of the biopsy procedure. For example, in a particular exemplary embodiment, after rough and/or manual positioning of the robotic arm 25 and end effector 29 adjacent the patient breast 35 such as via the user input on the control system 2000, with or without monitoring by the vision system 400, the vision system 400 subsequently determines the location of the end effector 29 and/or needle tip 31 relative to the ROI 37 and uses this information to operate the robotic arm 25 and finally position the end effector 29 and tip 31 in the end pose or pre-firing position to align the needle 27 with the ROI 37.

Referring now to FIGS. 2A-3C, the cameras/camera pairs 402, 410 can be secured to the gantry 10 at various locations in either fixed positions or positions that are moveable with respect to the gantry 10, or a combination thereof. With reference to the present disclosure, cameras/camera pairs 402, 410 designated as being fixed are cameras/camera pairs 402, 410 that are secured to the gantry 10 in a manner that cameras/camera pairs 402, 410 remain stationary with respect to the detector 40, and those designated as being moveable or mobile are cameras/camera pairs 402, 410 that are moveable relative to the detector 40. With regard to either embodiment, as it is necessary to know the location of the camera/camera pair 402, 410 with regard to the gantry 10, this location is determined either by mechanical design, i.e., the mounting position of the camera/camera pair 402, 410 and optional rotation encoder, or by registration, where the camera/camera pair 402, 410 views a pattern/markers on the gantry 10 and can determine their position using the view of the pattern/markers with regard to the gantry 10, though other marker-less methods for location determination can also be employed.

The position where the cameras/camera pairs 402, 410 are to be mounted on the gantry 10 is determined based on the monitored volume 200 that is required to be in view of the cameras/camera pairs 402, 410 and in which the robotic arm 25, biopsy device 28 and optionally the patient breast 35 are located. This monitored volume 200 accommodates the entire range of motion of the robotic arm 25 and biopsy device 28 with respect to the patient breast 35, such that the cameras/camera pairs 402, 410 can locate and determine the exact position of the robotic arm 25 and biopsy device 28 at all positions during the biopsy procedure.

Figure 2A:
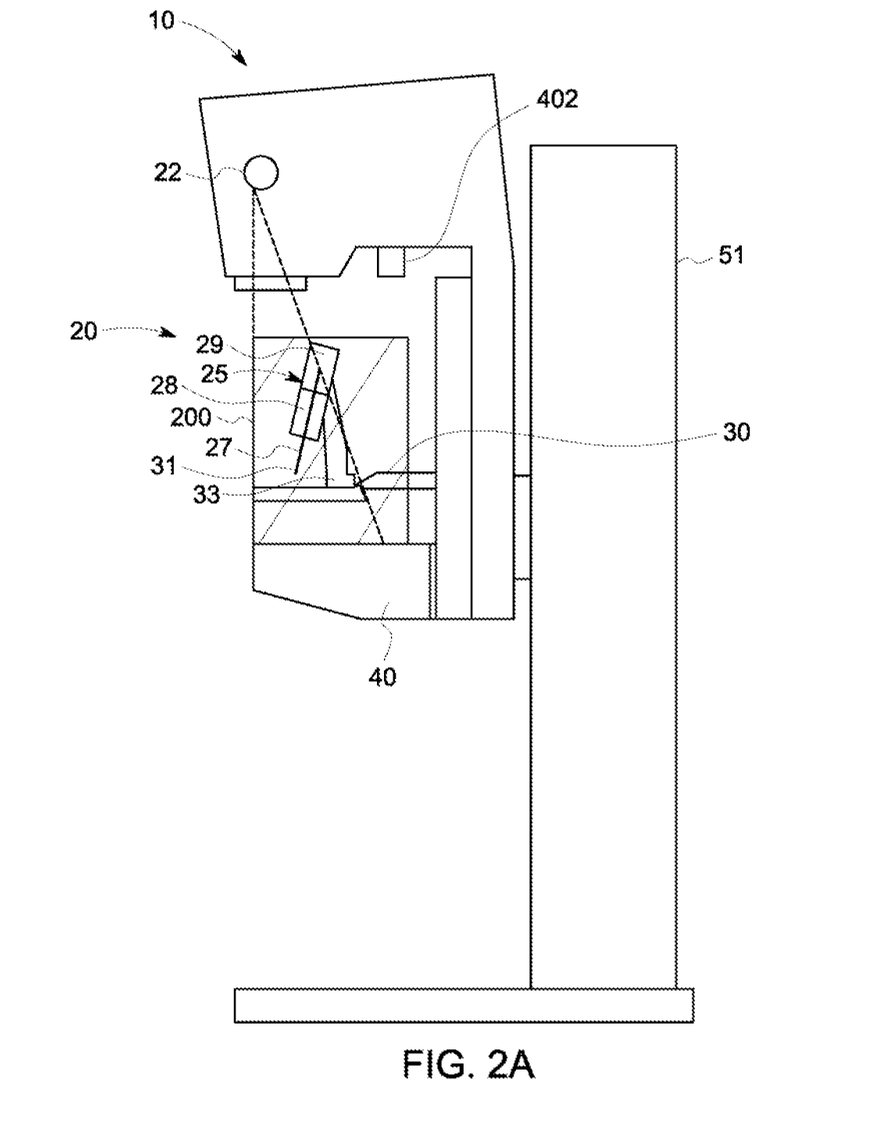
FIG. 2A is a schematic side elevation view of the mammography system of FIG. 1 illustrating the monitored volume to be viewed by the vision guided biopsy system.
Figure 2B:
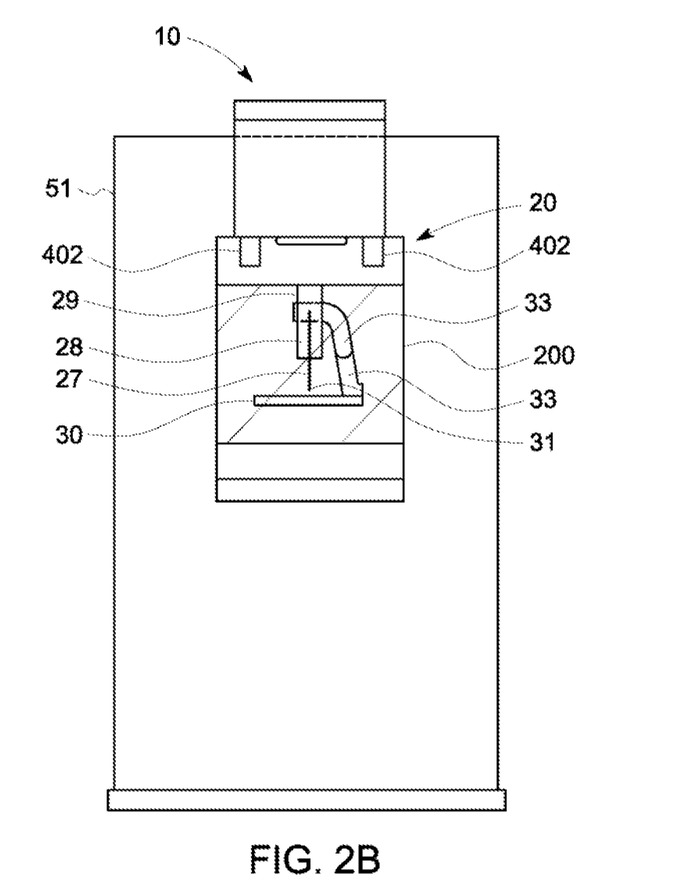
FIG. 2B is a schematic front elevation view of the mammography system of FIG. 1 illustrating the monitored volume to be viewed by the vision guided biopsy system.
Figure 2C:
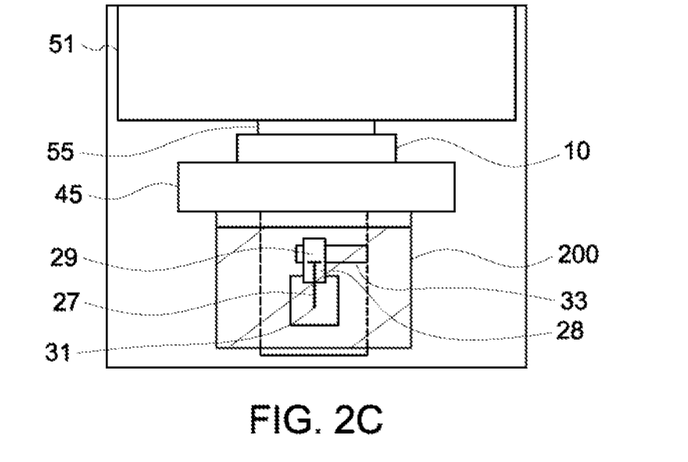
FIG. 2C is a schematic top elevation view of the mammography system of FIG. 1 illustrating the monitored volume to be viewed by the vision guided biopsy system.

In the exemplary embodiment of FIGS. 2A-2C showing the mammography system 1000 (with the casing 20 omitted in FIG. 2C), the monitored volume 200 is defined by the parallelepipedal volume bound by the front and rear sides of the detector 40, twice the lateral extension of the biopsy device 28 supported by the robotic arm 25 fixed on the compression paddle 30 when placed in a horizontal position, and the total height of the biopsy device 28 supported by the holder fixed on the compression paddle placed in vertical position plus the variable thickness of the patient's breast 35.

Within this defined monitored volume 200, depending of the quality of the location monitoring required, in one mode the cameras/camera pairs 402, 410 of the vision system 400 can be operated to monitor the position of the biopsy device 28 and/or the robotic arm 25/end effector 29, with the control system 2000 relying on the motive mechanism(s) incorporated on/within the segments 33 of the robotic arm 25 to precisely control the movement and location of the biopsy device 28/needle 27/needle tip 31, both at the initial localization point before starting the biopsy procedure and during the biopsy operation. With a need for increased location monitoring quality, in a another mode the vision system 400 can be operated to monitor the position of both the end effector 29 and the biopsy device 28/needle 27/needle tip 31 without reliance on any data from the robotic arm 25 regarding the position of the biopsy device 28 and the needle tip 31.

Figure 3A:
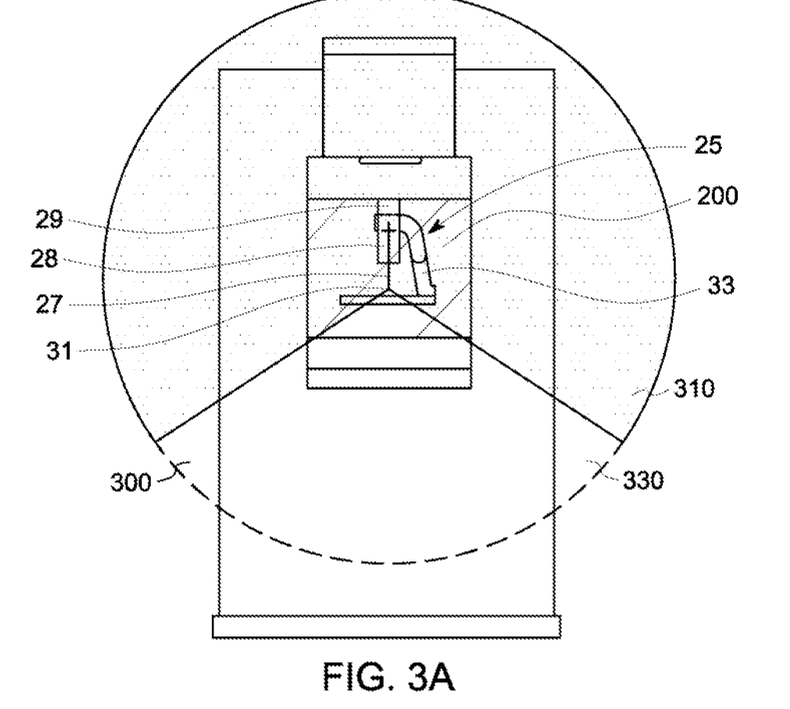
FIG. 3A is a schematic front elevation view of the mammography system of FIG. 1 illustrating the placement volume within which the vision system of the vision guided biopsy system can be positioned.
Figure 3B:
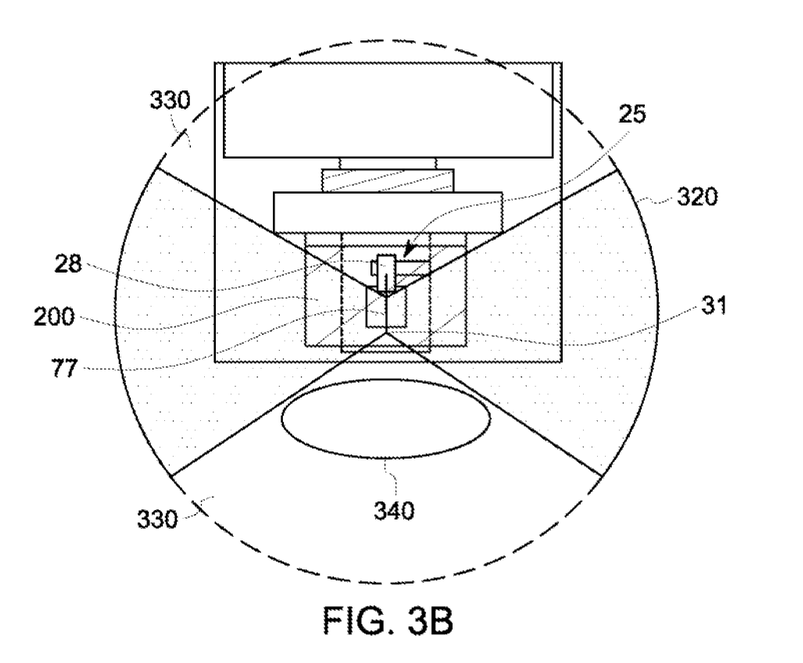
FIG. 3B is a schematic top elevation view of the mammography system of FIG. 1 illustrating the placement volume within which the vision system of the vision guided biopsy system can be positioned.

Referring now to FIGS. 3A-3B, with the volume 200 defined in which the entirety of the robotic arm 25 and biopsy device 28 to be viewed by the vision system 400 are located, it subsequently can be determined in what areas around the system 1000 the cameras/camera pairs 402, 410 can be positioned, and in what manners, e.g., fixed or mobile/moveable, in order to provide the images required for the positional determination of the robotic arm 25/end effector 29 and/or biopsy device 28/needle tip 31.

To provide the required views of the monitored volume 200, the vision system 400 of the present disclosure can be formed with three implementation variations with regard to the configuration of the cameras/camera pairs 402, 410: 1) moveable cameras/camera pairs 402, 410; 2) fixed cameras/camera pairs 402, 410; or 3) a combination of moveable and fixed cameras/camera pairs 402, 410. However, regardless of the particular configuration for the cameras/camera pairs 402, 410 of the vision system 400, it is necessary to determine the areas around and/or within the volume 200 in which the cameras/camera pairs 402, 410 can be positioned to have clear view of the volume 200 to obtain the required images. To make this determination, initially the distance a particular camera 402 in the vision system 400 can be positioned from the volume 200 in order to achieve the desired image of the robotic arm 25 and biopsy device 28 is ascertained. To do so, the distance is identified by a monitoring sphere 300 centered in the middle of the monitored volume 200 where the radius of the monitoring sphere 300 is defined by: 1) the magnification range of the camera 402; and 2) the combined optic and sensor resolution of the camera 402, where the goal is a resolution of +/−1 mm for the position of the needle 27 and/or needle tip 31. As schematically illustrated in the exemplary embodiments of FIGS. 3A-3B, with the known radius of the sphere 300 in which the camera cameras/camera pairs 402, 410 can be positioned, the shape of a camera placement or location volume 310 (viewed from the front), 320 (viewed from the top) in which the cameras/camera pairs 402, 410 can be placed for obtaining images of the robotic arm 25, biopsy device 28 and/or components thereof can subsequently be determined. This volume 310, 320 will be a reduction of the volume of the sphere 300 that accommodates for position exclusion zones 330 created by obstructions at various locations around and/or within the volume 310, 320 that prevent the placement of the camera at certain locations within the volume 310, 320. These obstructions creating the exclusion zones 330 can include, but are not limited to shadows of different pars/elements of the system 1000, such as one or more of the casing 20, detector 40, robotic arm 25, biopsy device 28, compression paddle 30 and paddle support device 45, among other components of the system 1000, as well as the trajectory(ies) of the X-rays 15 from the X-ray source 22, and/or the shadow of the patient 340 and any technician/physician (not shown) that may also be present around the system 1000. As individual procedures using the system 1000 and biopsy system 20 will have different operational parameters due to variances in the examination or procedure being performed, such as the number of X-ray images and/or number of biopsies required, and/or the size of the patient, among others, the determination of the exclusion zones 330 creating the reduction of the sphere 300 to define the camera placement volume 310, 320 can be defined manually and/or by the control system 2000 on a procedure by procedure basis. However, once the exclusion zones 330 and camera placement volume 310, 320 are determined in whatever manner desired, the exact position(s) of the camera cameras/camera pairs 402, 410 for the procedure within the volume 310, 320 can be made. Further, if the location of the obstruction(s) changes as a result of the components of the system 1000 moving during different steps of phases of the procedure being performed, the control system 2000 can determine the exclusion zones 330 at each step in order to define the camera placement volume 310, 320 associated with each step of the process to enable accurate location determination of the robotic arm 25/end effector 29 and/or biopsy device 28/needle tip 31 by the vision system 400.

With regard to the embodiment where the vision system 400 includes only moveable cameras cameras/camera pairs 402, 410, each camera/camera pair 402, 410 may independently need to move or be repositioned at each step of the biopsy procedure in order to maintain an unobstructed view of the monitored volume 200 as result of the movement of the components of the system 1000 to determine the exact position of the robotic arm 25/end effector 29 and/or biopsy device 28/needle tip 31. The movement for the camera/camera pair 402, 410 whether manually controlled or controlled by the control system 2000, is predetermined based on the placement or location volume 310, 320 defined by obstruction(s)/exclusion zones 330 present during the particular configuration of the system 1000 during the steps or phases of the biopsy procedure. In one exemplary embodiment, to limit the number of exclusion zones 330 that need to be addressed, as the X-ray source 22 is used only during imaging mode for the biopsy procedure, the casing 20 can be utilized as a support for a mobile camera/camera pair 402, 410 of the vision system 400, removing the casing 20 as a potential obstruction. Alternatively, or in conjunction with the movement of the camera(s) 402, 410, the X-ray source 22 can be moved from an imaging position to a parking position to allow the removal of the X-ray source 22 as an obstruction within the camera placement volume 310, 320.

Further, with regard to the manner of operation of the embodiment of the vision system 400 including one or more moveable cameras/camera pairs 402, 410, once the moveable camera/camera pair 402, 410 is disposed in the appropriate position in the placement or location volume 310, 320, it is necessary to initially operate the camera/camera pair 402, 410 to obtain an image, such as in a stereoscopic manner to generate a 3D image of the location of the camera/pair of cameras 402, 410 using the other camera(s) 402, 410 of the vision system 400, to locate the position of the camera/camera pair 402, 410 with respect to a fixed part of the system 1000. By determining the position of the camera/camera pair 402, 410 relative to the known position of at least a part of the system 1000, such as the location of the component of the system 1000 to which the camera/camera pair 402, 410 is mounted, the location of the camera 402, 410 can be utilized in subsequent stereoscopic processes for the determination of the location of the robotic arm 25/end effector 29 and/or biopsy device 28/needle tip 31 robotic arm 25/end effector 29 and/or biopsy device 28/needle tip 31 in the biopsy procedure. Further, while the position of the camera/camera pair 402, 410 can also be ascertained as a result of the determination of the position for the camera/camera pair 402, 410 within the volume 310, 320 as discussed previously, due to the tolerance requirements for the positional accuracy of the location of the needle tip 31, any variations in the exact location of the camera/camera pair 402, 410 resulting from variances in the support structure, such as due to the angle of any support structure (not shown) holding the camera/camera pair 402, 410 for the camera/camera pair 402, 410 can be compensated for by using the camera/camera pair 402, 410 to exactly locate the camera/camera pair 402, 410 relative to the system 1000. Once the location of the camera/camera pair 402, 410 is determined, the camera/camera pair 402, 410 can subsequently be operated in a subsequent stereoscopic process to define the position of the robotic arm 25/end effector 29 and/or biopsy device 28/needle tip 31 during performance of the biopsy procedure.

Figure 4A:
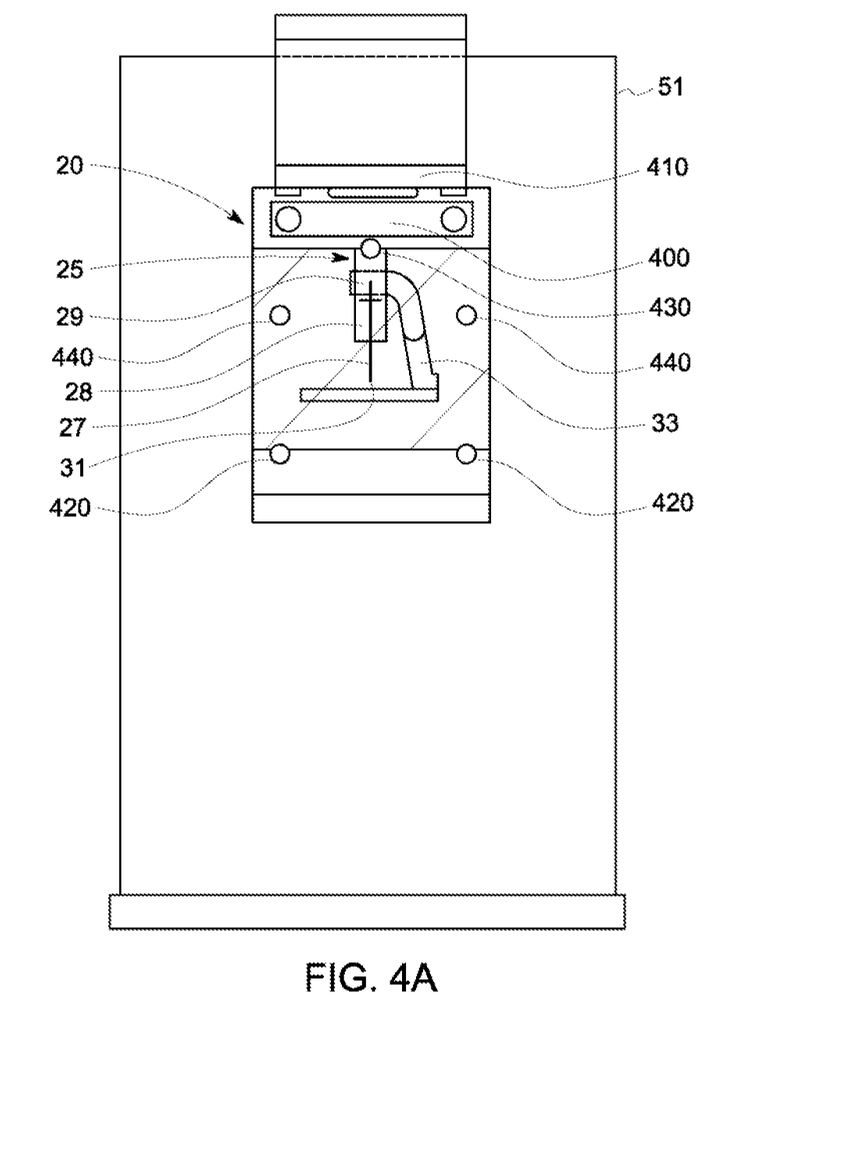
FIG. 4A is a schematic front elevation view of the mammography system of FIG. 1 illustrating an exemplary embodiment of alternative locations of the vision system components of the vision guided biopsy system and vision system reference points.
Figure 4B:
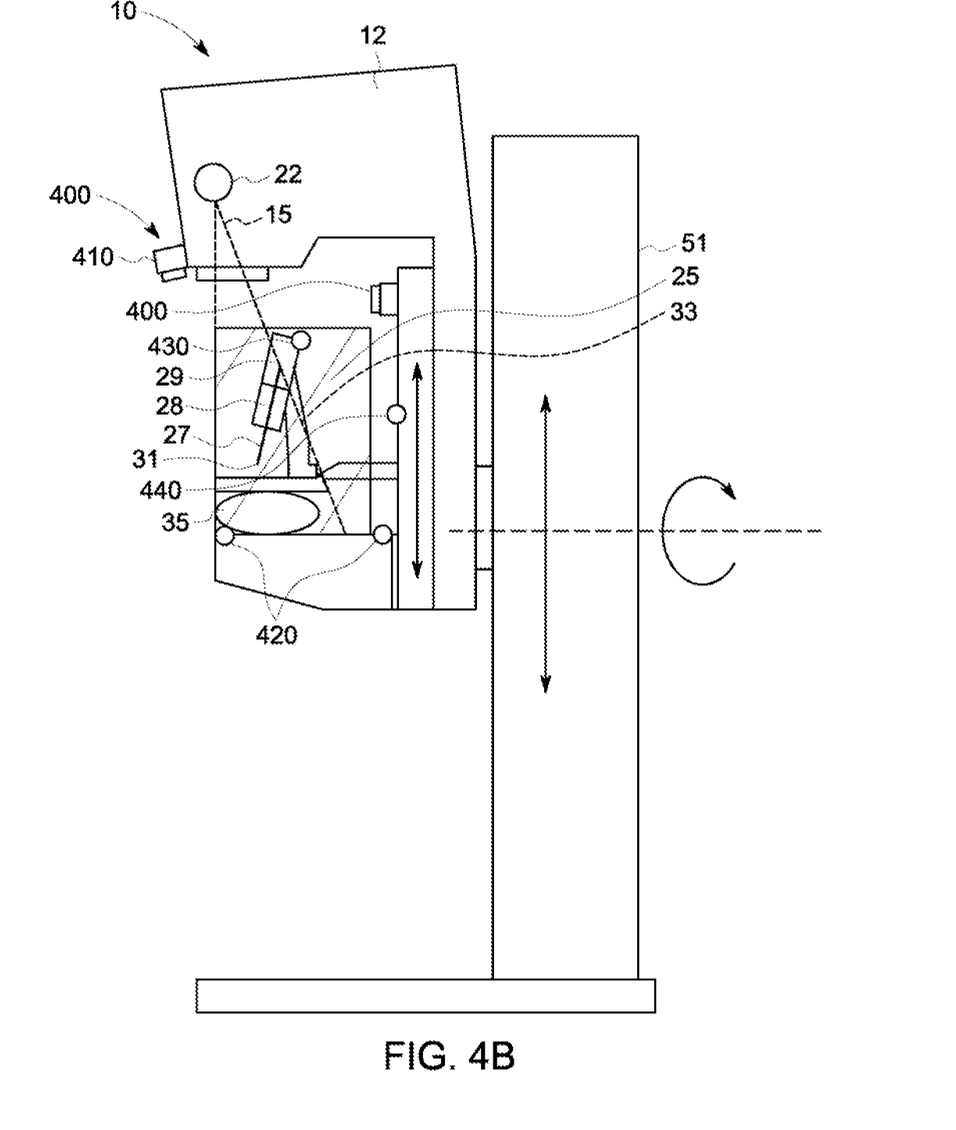
FIG. 4B is a schematic side elevation view of the mammography system of FIG. 1 illustrating an exemplary embodiment of alternative locations of the vision system components of the vision guided biopsy system and vision system reference points.

Alternatively, as shown in FIGS. 4A-4B, instead of taking an image or images of the system 1000/gantry 10 to determine the exact position of a camera/camera pair 402, 410 using a stereoscopic process, the system 1000 can include reference points 420, 430, 440 located on the gantry 10. The reference points 420, 430, 440 can be formed as optical targets readily located by the camera/camera pair 402, 420 and have positions that are mechanically defined either by the construction of the gantry 10/system 1000 or by indexed mechanical moves, e.g., mechanical design and/or encoder values. By obtaining an image of a number of the reference points 420, 430, 440, the location of the camera/camera pair 402, 410 can be determined using the image of the reference points 420, 430, 440 and the known location of the reference points 420, 430, 440 on the gantry 10/system 1000. As shown in FIGS. 4A and 4B, the reference points 420, 440 can be disposed in multiple locations on the front or side of certain portions of the gantry 10, such as a detector 40 and the paddle support/movement mechanism 45. Additionally, reference points 430 can be disposed on the robotic arm 25/end effector 29 and/or biopsy device 28, such as on the top of the robotic arm 25, to allow for easier monitoring of the position of the device 28 based on the known location of the reference point 430 on the arm 25, or other part of the biopsy device 28.

In other embodiments for the vision system 400, the cameras/camera pairs 402, 410 can be disposed in fixed mounting locations that do not move relative to the system 1000. One configuration for the fixed cameras/camera pairs 402, 410 involves placing the cameras/camera pairs 402, 410 on a ceiling or other mounting surface (not shown) located directly above the system 1000. Provided that the distance between ceiling and the robotic arm 25/end effector 29 and/or biopsy device 28/needle tip 31 within the volume 200, falls within the placement volume 310, 320 defined by the camera resolution and the exclusion zones 330 defined by any obstructions, a direct ceiling mount of a fixed cameras/camera pairs 402, 410 above the robotic arm 25/end effector 29 and/or biopsy device 28/needle tip 31 can be employed. In an alternative exemplary embodiment, the cameras/camera pairs 402, 410 can be mounted in fixed positions to portions of the gantry 10, and/or the stand 51, as desired.

In another, exemplary embodiment, the fixed mounting of the cameras/camera pairs 402, 410 can be done directly on the gantry 10. In this configuration the camera 402, 410 is secured to a part of the gantry 10 with a known position relative to the detector 40 and to the image referential or plane in which the target ROI 37 to be biopsied is located. If there is no camera calibration performed using images from the camera/camera pairs 402/410, then the camera has to be fixed with regards to the detector 40 and image plane in which is the lesion/ROI 37 coordinates are disposed in order to provide the necessary positional information from the images. With regard to the position of the cameras/camera pairs 402, 410 on the gantry 10, any suitable position can be utilized that falls within the placement volume 310, 320, such as on the paddle support mechanism 45.

In still another exemplary embodiment of the biopsy system 23 including the vision system 400, the cameras/camera pairs 402, 410 can be mounted in a combination fixed and moveable configuration, with one camera/camera pair 402, 410 disposed in a fixed position, such as those described previously, and at least one other camera/camera pair 402, 410 disposed in a moveable position. In one example of this configuration, the fixed camera/camera pair 402 is disposed in a location where the fixed camera/camera pair 402, 410 can monitor the location of the robotic arm 25/end effector 29 and/or biopsy device 28/needle tip 31 (though a separate, second fixed camera/camera pair 402, 410 positioned on the system 1000 can be utilized to monitor the location of the needle tip 31), while the moveable or mobile camera/camera pair 402, 410 is operated to only track the location of the needle tip 31. In one specific exemplary embodiment shown in FIGS. 4A and 4B, which can be utilized during exploratory evaluation biopsy procedure, a fixed camera/camera pair 402, 410 is located on the paddle support mechanism 45 and combined with a moveable camera/camera pair 402, 410 located on a front surface of the casing 20.

In operation of the mammography system 1000 including the biopsy system 23 including the robotic arm 25/end effector 29 and biopsy device 28/needle tip 31 and vision system 400, initially the vision system 400 is calibrated for use with the system 1000. To do so, in one exemplary embodiment, a phantom (not shown) including ROIs at known positions within the phantom is placed on the detector 40. After operating the system 1000 in an imaging mode to detect an ROI within the phantom, the vision system 400 is operated to detect the same known position in the camera referential and then compute the camera position in regards to the image referential. In an alternative method, After operating the system 1000 in an imaging mode to detect an ROI within the phantom, the vision system 400 is operated to move the robotic arm 25 to position the biopsy device 28 into a pre-firing/end stop position and the alignment of the needle tip 31 with the selected ROI can be checked. In an alternative method, the vision system 400 can be calibrated by first moving the robotic arm 25 to different positions. At each position the vision system 400 is operated to locate the end-pose of the robotic arm 25, i.e., the end effector 29 and/or needle tip 31, with the location of the end pose for each position compared with the location determined for the end pose in an X-ray image(s) taken at the same position for the robotic arm 25.

After the calibration of the vision system 400, when in use to perform a biopsy procedure after an imaging procedure conducted by the mammography system 1000 to identify an ROI 37 within the patient breast 35, initially the robotic arm 25 is operated to coarsely, e.g., manually, position the end effector 29 near the patient breast 35 in an initial end pose. This movement can be controlled by the control system 2000 optionally under the direction or guidance of the vision system 400, or can be done manually by the user through the user interface. Once disposed adjacent the patient breast 35 in the initial end pose, any passive segments 33 of the robotic arm 25 are locked or disabled from further movement using brakes (not shown) on the arm 25 that can be manually or automatically engaged to eliminate movement of the arm 25 and optionally end effector 29 other than under the control of the control system 2000 and vision system 400.

After the robotic arm 25 is prepared, the vision system 400 is operated to take images of the end effector 29 and/or needle tip 31 using the cameras/camera pairs 402, 410. The images are utilized in a stereoscopic/computer stereo vision process to create a 3D image of the end effector 29, biopsy device 28 and/or needle tip 31, thus defining the position of the end effector 29, biopsy device 28 and/or needle tip 31 relative to the target ROI 37. With the location of the ROI 37 to be biopsied within the patient breast 35 already known within the 3D image dataset of the patient breast 35 created from a prior X-ray imaging procedure, the location of the end effector 29, biopsy device 28 and needle tip 31 from the vision system 400 can be correlated with the ROI location determined by the x-ray imaging system.

With the relative positions of the end effector 29, biopsy device 28 and needle tip 31 and the ROI 37 known, the vison system 400 can operate the motive mechanisms on the robotic arm 25 to move the end effector 29 from the initial end pose precisely to the desired final end pose/pre-firing position for the biopsy device 28 and needle tip 31. As the robotic arm 25 is moved under the guidance of the vision system 400, the vision system 400 continuously obtains images of the end effector 29, biopsy device 28 and/or needle tip 31 in order to determine the progress of the needle tip 31 to the desired final end pose. The fine motion of the robotic arm 25 under the control of the vision system 400 can be corrected based on the updated images obtained by the cameras/camera pairs 402, 410 to ensure the alignment of the needle tip 31 remains within the +/−1 mm tolerance required for the biopsy procedure.

Alternatively, the robotic arm 25 can be moved into the final end pose/pre-firing position manually, while still under the guidance of the vision system 400. In this embodiment, feedback regarding the operator movement of the robotic arm 25 can be provided from the vision system 400 based on the continuous monitoring of position of the end effector 29, biopsy device 28 and/or needle tip 31 by the vision system 400 relative to the patient breast 35/ROI 37 to enable the operator to correct the movement of the robotic arm 25 within the required tolerance. The feedback can be provided by the vision system 400 in any suitable manner, e.g., braking of the robotic arm 25 to provide force feedback, haptic feedback through the user input for controlling the robotic arm 25, and/or notifications on the display for the system 1000, among others. After automatically or manually positioning the biopsy device 28 and needle tip 31 in the desired final end pose position under the guidance of the vision system 400, the biopsy device 28 can be operated to perform the biopsy.

The use of the camera(s)/camera pair(s) 402, 410 by the vision system 400 to precisely define the position of the end effector 29, biopsy device 28 and/or needle tip 31 at the initial end pose location is performed with a sufficient accuracy to verify that any further movement of the end effector 29 under the control of the vision system 400 is also done with an accuracy sufficient to place the needle tip 31 in the expected position against or within the patient breast 35 when moving the needle tip 31 from an idle position into a pre-fire position, for example. In addition, with this level of accuracy, the position tracking by the camera(s)/camera pair(s) 402, 410 of the vision system 400 can be used to continuously track the position of all parts of the robotic arm 25 and biopsy device 28, e.g., the position of the mechanical components 33 of the arm 25, either individually or collectively, such that their position(s) can be corrected in real time during the entire biopsy procedure. Further, even though the vision system 400 cannot monitor the position of the needle tip 31 when disposed within the patient breast 35, the combined knowledge of the length of the needle 27 and planned movement of the end effector 29, and thus the biopsy device 28 to which the needle 27 is connected, can be used to determine the length of the inserted portion of the needle 27.

In other alternative embodiments, in addition to the camera/camera pairs 402, 410, the vision system 400 can include sensors (not shown) that are disposed on the robotic arm 25 and/or biopsy device 28. The sensors, which can include but are not limited to various position sensors, such as one or more inclinometers disposed on the robot arm 25, such as on one or more segments 33 and/or the end effector 29, for example.

This positioning of the biopsy device 28 and the robotic arm 28/end effector 29 on the compression paddle 30, or in other previously unusable locations on the gantry 10, is enabled by the ability to significantly reduce the weight of the components forming the robotic arm 25, due to the relaxed requirements or constraints on the accuracy of the movement of the robotic arm 25 due to the employment of the vision system 400. With the lighter robotic arm 25, the vision system 400 is able to control movement of the robotic arm 25 during biopsy procedure with the accuracy required to achieve the desired results, similar to the prior art biopsy devices.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A method for guiding a biopsy system while performing a biopsy procedure, the method comprising the steps of:
   providing a mammography system comprising:
      a gantry disposed on a support surface and including an X-ray source, an X-ray detector alignable with the X-ray source, and a compression paddle moveable relative to the X-ray detector to secure a patient breast therebetween;
      a biopsy system mounted to the gantry, the biopsy system including a movable robotic arm secured to the gantry, and a biopsy device disposed on the robotic arm opposite the gantry, the biopsy device including a biopsy needle operably connected to the biopsy device opposite the robotic arm;
      a control system operably connected to the gantry to control operation of the X-ray source and X-ray detector to generate X-ray image data in an imaging mode of the mammography system, and to control operation of the biopsy system in a biopsy mode of the mammography system, the control system including a central processing unit and interconnected database for processing the X-ray image data from the X-ray detector, a display operably connected to the control system for presenting information to a user, and a user interface operably connected to the control system to enable user input to the control system; and
      a vision guidance system disposed on the gantry and operably connected to the control system, the vision guidance system including at least one camera operable to generate images of the robotic arm and the biopsy device and the biopsy needle to guide movement of the biopsy system;
   positioning a patient breast between the X-ray detector and the compression paddle;

generating X-ray image data during the imaging mode;
determining a region of interest within the patient breast using the generated X-ray image data;
obtaining a number of images of the robotic arm and the biopsy device and biopsy needle with the vision guidance system;
determining a position of the biopsy system relative to the region of interest from the number of images;
computing a movement direction based on the position of the biopsy system relative to the region of interest; and
moving the robotic arm and the biopsy device and the biopsy needle towards the region of interest based on the movement direction.

2. The method of claim 1, further comprising the step of determining a placement volume for the positioning of the at least one camera prior to positioning the patient breast between the X-ray detector and the compression paddle.

3. The method of claim 1, wherein the at least one camera comprises at least one pair of cameras and wherein the step of obtaining the number of images comprises the steps of:
obtaining a number of pairs of images from the at least one pair of cameras; and
processing the number of pairs of images in a stereoscopic process to generate a 3D image of the location of the robotic arm.

4. The method of claim 2, wherein the step of determining the placement volume comprises the steps of:
determining a monitored volume on the gantry;
determining a monitoring sphere around the monitored volume;
determining locations of obstructions within the monitoring sphere that prevent imaging of the monitored volume by the vision guidance system; and
defining exclusion zones within the monitoring sphere based on the location of the obstructions, wherein the exclusion zones modify the monitoring sphere into the placement volume.

5. The method of claim 4, wherein the monitored volume is defined by a volume encompassing an entire range of motion of the biopsy device.

6. The method of claim 4, wherein the step of determining locations of obstructions within the monitoring sphere comprises determining the first locations of obstructions within the monitoring sphere during a first procedure step, and wherein the method further comprises the steps of:
determining second locations of obstructions within the monitoring sphere during a second procedure step; and
defining exclusion zones within the monitoring sphere for the second procedure step based on the location of the second obstructions, wherein the exclusion zones modify the monitoring sphere into the placement volume.

7. The method of claim 4, further comprising the step of placing the at least one camera within the placement volume.

8. The method of claim 5, wherein the monitoring sphere is defined by a magnification range of the at least one camera and a combined optic, a sensor resolution of the at least one camera, or a combination thereof, required to achieve a desired resolution for the at least one camera.

9. The method of claim 8, wherein the desired spatial resolution for the at least one camera is selected to enable positioning of the end effector within a positional tolerance of +/−1 mm.

10. The method of claim 7, wherein the placement of the at least one camera within the placement volume is a fixed camera placement, a moveable camera placement, or combinations thereof.

11. The method of claim 3, further comprising the step of manually moving the robotic arm towards the patient breast to an initial end pose position prior to obtaining the number of images.

12. The method of claim 11, further comprising the step of disabling manual movement of the robotic arm after manually moving the robotic arm.

13. The method of claim 11, wherein the step of moving the robotic arm comprises:
comparing a location of the robotic arm at the initial end pose location; and
operating the robotic arm to move a tip of the biopsy needle from the initial end pose position into a final end pose position.

14. The method of claim 13, wherein the step of operating the robotic arm comprises:
continuously obtaining images from the at least one camera pair to update the location of the robotic arm relative to the region of interest; and
moving the robotic arm to align the tip of the biopsy needle with the region of interest within a set tolerance range bade on the updated location of the robotic arm relative to the region of interest.

15. The method of claim 14, wherein the biopsy system is mounted to the compression paddle.

16. A mammography system operable in an imaging mode and in a biopsy mode, the system comprising:
a gantry disposed on a support surface and including an X-ray source, an X-ray detector alignable with the X-ray source, and a compression paddle moveable relative to the X-ray detector to secure a patient breast therebetween;
a biopsy system mounted to the gantry, the biopsy system including a movable robotic arm secured to the gantry, a biopsy device disposed on the robotic arm opposite the gantry, and a needle operably connected to the biopsy device opposite the robotic arm;
a control system operably connected to the gantry to control the operation of the X-ray source and X-ray detector to generate X-ray image data in an imaging mode for the mammography system, and to control the operation of the biopsy device in an biopsy mode for the mammography system, the control system including a central processing unit and interconnected database for processing the X-ray image data from the X-ray detector, a display operably connected to the control system for presenting information to a user, and a user interface operably connected to the control system to enable user input to the control system; and
a vision guidance system disposed on the gantry and operably connected to the control system, the vision guidance system including at least one camera operable to generate images of the biopsy system and to guide movement of the biopsy system based on a position of the biopsy system and X-ray image data.

17. The mammography system of claim 16, wherein the biopsy system is mounted to the compression paddle.

18. The mammography system of claim 16, wherein the at least one camera is mounted to the gantry via a fixed camera placement, a moveable camera placement, or combinations thereof.

19. The mammography system of claim 16, wherein the at least one camera comprises at least one pair of cameras capable of obtaining a number of pairs of images for use by the processing unit in a stereoscopic process to generate a 3D image of locations of the biopsy system.

20. The mammography system of claim 16, wherein the biopsy system is mounted to the X-ray detector.

\* \* \* \* \*